US008044066B2

(12) United States Patent
Dubois et al.

(10) Patent No.: US 8,044,066 B2
(45) Date of Patent: Oct. 25, 2011

(54) DERIVATIVES OF PYRROLOPYRIDINE-2-CARBOXAMIDES, PREPARATION THEREOF AND THERAPEUTIC APPLICATION THEREOF

(75) Inventors: Laurent Dubois, Paris (FR); Yannick Evanno, Paris (FR); Andrè Malanda, Paris (FR)

(73) Assignee: Sanofi-Aventis, Paris (FR)

( * ) Notice: Subject to any disclaimer, the term of this patent is extended or adjusted under 35 U.S.C. 154(b) by 283 days.

(21) Appl. No.: 12/504,770

(22) Filed: Jul. 17, 2009

(65) Prior Publication Data

US 2009/0298865 A1   Dec. 3, 2009

Related U.S. Application Data

(63) Continuation of application No. PCT/FR2008/000054, filed on Jan. 17, 2008.

(30) Foreign Application Priority Data

Jan. 19, 2007   (FR) ..................................... 07 00356

(51) Int. Cl.
*A61K 31/437* (2006.01)
*C07D 471/12* (2006.01)

(52) U.S. Cl. ......... 514/300; 546/112; 546/113; 514/299

(58) Field of Classification Search ................. 546/112, 546/113; 514/299, 300
See application file for complete search history.

(56) References Cited

U.S. PATENT DOCUMENTS 7,745,467 B2 *   6/2010   Dubois et al. ................. 514/339
7,763,636 B2 *   7/2010   Dubois et al. ................. 514/300

FOREIGN PATENT DOCUMENTS

| WO | WO 03/049702 | 6/2003 |
|---|---|---|
| WO | WO 03/068749 | 8/2003 |
| WO | WO 2004/104001 | 12/2004 |
| WO | WO 2005/080391 | 9/2005 |
| WO | WO 2006/059163 | 6/2006 |
| WO | WO 2006/089309 | 8/2006 |
| WO | WO 2007/088277 | 8/2007 |

OTHER PUBLICATIONS

Abramovitch, R. A., et. al., Microwave-Assisted Alkylations of Activated Methylene Groups, Synthetic Communications, (1995), vol. 25, No. 1, pp. 1-8.
Antilla, J. C. et al, The Copper-Catalyzed N-Arylation of Indoles, J. Am. Chem. 'Soc., vol. 124, No. 30, (2002), pp. 11684-11688.
Barberis. C., et. al., Cu(I)-Catalyzed intramolecular Cyclization of Ene-Carbamates: Synthesis of indoles and Pyrrole[2,3-c]Pyridines, Tetrahedron Letters, vol. 46, (2005), pp. 8877-8880.
Fagan, G. P., et. al., Indoline Analogues of Idazoxan: Potent a2-Antagonists and a1-Agonists, J. Med. Chem., (1988), vol. 31, pp. 944-948.
Fresneda, P. M., et. al., Synthetic Studies Towards the 2-Aminopyrimidine Alkaloids Variolins and Meridianins From Marine Chain, Tetrahedron Letters, vol. 41, (2000), pp. 4777-4780.
Frydman, B., et. al., Pyrroles From Azaindoles. A Synthesis of Porphobilinogen, J. Am. Chem. Soc., (1965), vol. 87, pp. 3530-3531.
Frydman. B., et. al., Synthesis of Substituted 4- and 6-Azaindoles, J.Org.Cnem., vol. 33, No. 10, (1968), pp. 3762-3766.
Furstner A., et. al., Ion-Catalyzed Cross-Coupling Reactions, J. Am Chem Soc., (2002), vol. 124. pp. 13856-13863.
Klapars, A., et. al., A General and Efficient Copper Catalyst for the Amidation of Aryl Halides and the N-Arylation of Nitrogen Heterocycles, J. Am. Chem, Soc., (2001) pp, 7727-7729 vol. 123.
Kolasa, T, et. al., Synthesis of Indolylalkoxyiminoalkylcarboxylates as Leukotriene Biosynthesis Inhibitors, Bioorganic & Medicinal Chemistry, vol. 5, No. 3, pp. 507-514, (1997).
Lachance, N., et. al., Rapid and Efficient Microwave-Assisted Synthesis of 4-, 5-. 6-, and 7-Azaindoles, Synthesis, (2005), vol. 15, pp. 2571-2577.
Lomberget, T., et. al., A Regioselective Route to 5- and 6-Azaindoles, Synlett, (2005), vol. 13, pp. 2080-2082.
Mitsunobu, O., et. al., The Use of Diethyl Azodicarboxylate and Triphenylphosphine in Synthesis and Transformation of Natural Products, Synthesis, (1981), pp. 1-28.
Nazare, M., et. al., A Flexible, Palladium-Catalyzed Indole and Azaindole Synthesis by Direct Annulation of Chloroanilines and Chloroaminopyridines With Ketones, Angew. Chem. Int. Ed., (2004), vol. 43, pp. 4526-4528.
Roy, P. J., et. al., The Hemetsberger-Knittel Synthesis of Substituted 5-, 6-, and 7-Azaindotes, Synthesis, (2005), vol, 16. pp. 2751-2757.
Trecourt, F., et al., First Syntheses of Caerulomycin E and Collismycins A and C. A New Synthesis of Caerulomycin A, J. Org. Chem., (1998). vol. 63, pp. 2892-2897.
Yakhontov, L. N., et. al., About Reactivity of Isomeric Azaindoles, Tetrahedron Letters, No. 24, pp. 1909-1912, (1969).

* cited by examiner

*Primary Examiner* — Golam M Shameem
(74) *Attorney, Agent, or Firm* — Scully, Scott, Murphy & Presser, P.C.

(57) ABSTRACT

The invention relates to compounds of formula (I):

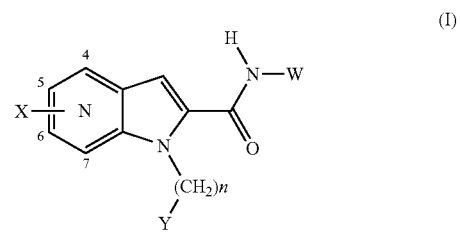

Wherein n, the pyrrolopyridine core, X, Y and W are as described herein. The invention also relates to a preparation method and to a therapeutic application.

23 Claims, No Drawings

DERIVATIVES OF PYRROLOPYRIDINE-2-CARBOXAMIDES, PREPARATION THEREOF AND THERAPEUTIC APPLICATION THEREOF

CROSS REFERENCE TO RELATED APPLICATIONS

This application is a continuation of International application No. PCT/FR2008/000,054, filed Jan. 17, 2008, which is incorporated herein by reference in its entirety; which claims the benefit of priority of French Patent Application No. 07/00, 356, filed Jan. 19, 2007.

BACKGROUND OF THE INVENTION

Field of the Invention

The invention relates to compounds derived from N-heteroaryl-1-heteroarylalkyl-1H-pyrrolopyridine-2-carboxamides and N-heteroaryl-1-heteroaryl-1H-pyrrolopyridine-2-carboxamides, which show in vitro and in vivo antagonist activity on receptors of TRPV1 (or VR1) type.

A first subject of the invention relates to compounds corresponding to the general formula (I) below.

Another subject of the invention concerns processes for preparing the compounds of general formula (I).

Another subject of the invention concerns the use of the compounds of general formula (I) especially in medicaments or in pharmaceutical compositions.

SUMMARY OF THE INVENTION

The compounds of the invention correspond to the general formula (I):

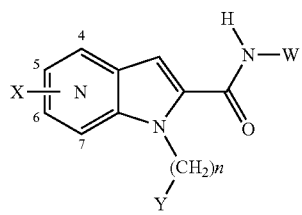

(I)

in which
n is equal to 0, 1, 2 or 3;
the pyrrolopyridine nucleus is a pyrrolo[3,2-b]pyridine group, a pyrrolo[3,2-c]pyridine group, a pyrrolo[2,3-c]pyridine group or a pyrrolo[2,3-b]pyridine group; the pyrrolopyridine nucleus being optionally substituted in the carbon position 4, 5, 6 and/or 7 with one or more substituents X, which may be identical or different, chosen from a halogen atom and $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkoxy, $C_3$-$C_7$-cycloalkyl-$C_1$-$C_3$-alkylene-O—, $C_1$-$C_6$-fluoroalkoxy, cyano, C(O)$NR_1R_2$, nitro, $NR_1R_2$, $C_1$-$C_6$-thioalkyl, —S(O)—$C_1$-$C_6$-alkyl, —S(O)$_2$—$C_1$-$C_6$-alkyl, $SO_2NR_1R_2$, $NR_3COR_4$, $NR_3SO_2R_5$, aryl, aryl-$C_1$-$C_5$-alkylene, heteroaryl and heteroaryl-$C_1$-$C_5$-alkylene groups, the aryl or the heteroaryl being optionally substituted with one or more substituents chosen from a halogen atom and $C_1$-$C_6$-alkyl, $C_3$-$C_7$-cycloalkyl, $C_3$-$C_7$-cycloalkyl-$C_1$-$C_3$-alkylene-O—, $C_1$-$C_6$-fluoroalkyl, $C_1$-$C_6$-alkoxy, $C_3$-$C_7$-cycloalkoxy, $C_3$-$C_7$-cycloalkyl-$C_1$-$C_3$-alkylene-O—, $C_1$-$C_6$-fluoroalkoxy, nitro or cyano groups;

Y represents a heteroaryl optionally substituted with one or more groups chosen from a halogen atom and $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, hydroxyl, $C_1$-$C_6$-alkoxy, $C_3$-$C_7$-cycloalkoxy, $C_3$-$C_7$-cycloalkyl-$C_1$-$C_6$-alkylene-O—, $C_1$-$C_6$-fluoroalkoxy, cyano, C(O)$NR_1R_2$, nitro, $NR_1R_2$, $C_1$-$C_6$-thioalkyl, $C_1$-$C_6$-thiofluoroalkyl, thiol, —S(O)—$C_1$-$C_6$-alkyl, —S(O)—$C_3$-$C_7$-cycloalkyl, —S(O)—$C_1$-$C_6$-alkylene-$C_3$-$C_7$-cycloalkyl, —S(O)$_2$—$C_1$-$C_6$-alkyl, —S(O)$_2$—$C_3$-$C_7$-cycloalkyl, —S(O)$_2$—$C_1$-$C_6$-alkylene-$C_3$-$C_7$-cycloalkyl, $SO_2NR_1R_2$, $NR_3COR_4$, $NR_3SO_2R_5$, aryl, aryl-$C_1$-$C_5$-alkylene, heteroaryl or heteroaryl-$C_1$-$C_5$-alkylene groups, the aryl or the heteroaryl being optionally substituted with one or more substituents chosen from a halogen and $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkoxy, $C_3$-$C_7$-cycloalkyl-$C_1$-$C_6$-alkylene-O—, $C_1$-$C_6$-fluoroalkoxy, nitro or cyano groups;

$R_1$ and $R_2$, represent, independently of each other, a hydrogen atom or a $C_1$-$C_6$-alkyl, $C_3$-$C_7$-cycloalkyl, $C_3$-$C_7$-cycloalkyl-$C_1$-$C_3$-alkylene, aryl, aryl-$C_1$-$C_5$-alkylene, heteroaryl or heteroaryl-$C_1$-$C_5$-alkylene group, the aryl or the heteroaryl being optionally substituted with one or more substituents chosen from a halogen and $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkoxy, $C_3$-$C_7$-cycloalkyl-$C_1$-$C_6$-alkylene-O—, $C_1$-$C_6$-fluoroalkoxy, nitro or cyano groups;

or $R_1$ and $R_2$ form, together with the nitrogen atom that bears them, an azetidine, pyrrolidine, piperidine, azepine, morpholine, thiomorpholine, piperazine or homo-piperazine group, this group being optionally substituted with a $C_1$-$C_6$-alkyl, $C_3$-$C_7$-cycloalkyl, $C_3$-$C_7$-cycloalkyl-$C_1$-$C_3$-alkylene, aryl, aryl-$C_1$-$C_5$-alkylene, heteroaryl or heteroaryl-$C_1$-$C_5$-alkylene group, the aryl or the heteroaryl being optionally substituted with one or more substituents chosen from a halogen and $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkoxy, $C_3$-$C_7$-cycloalkyl-$C_1$-$C_6$-alkylene-O—, $C_1$-$C_6$-fluoroalkoxy, nitro or cyano groups;

$R_3$ and $R_4$ represent, independently of each other, a hydrogen atom or a $C_1$-$C_6$-alkyl, $C_3$-$C_7$-cycloalkyl, $C_3$-$C_7$-cycloalkyl-$C_1$-$C_3$-alkylene, aryl, aryl-$C_1$-$C_5$-alkylene, heteroaryl or heteroaryl-$C_1$-$C_5$-alkylene group, the aryl or the heteroaryl being optionally substituted with one or more substituents chosen from a halogen and $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkoxy, $C_3$-$C_7$-cycloalkyl-$C_1$-$C_6$-alkylene-O—, $C_1$-$C_6$-fluoroalkoxy, nitro or cyano groups;

$R_5$ represents a $C_1$-$C_6$-alkyl, $C_3$-$C_7$-cycloalkyl, $C_3$-$C_7$-cycloalkyl-$C_1$-$C_3$-alkylene, aryl, aryl-$C_1$-$C_5$-alkylene, heteroaryl or heteroaryl-$C_1$-$C_5$-alkylene group, the aryl or the heteroaryl being optionally substituted with one or more substituents chosen from a halogen and $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkoxy, $C_3$-$C_7$-cycloalkyl-$C_1$-$C_6$-alkylene-O—, $C_1$-$C_6$-fluoroalkoxy, nitro or cyano groups;

W represents a fused bicyclic group of formula:

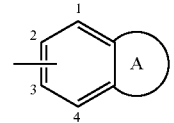

linked to the nitrogen atom via positions 1, 2, 3 or 4;
A represents a 5- to 7-membered heterocycle comprising from one to three heteroatoms chosen from O, S and N;
the carbon atom(s) of A being optionally substituted with one or more groups chosen from a hydrogen atom and $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl, aryl-$C_1$-$C_5$-alkylene, heteroaryl or heteroaryl-$C_1$-$C_5$-alkylene, oxo or thio groups; the aryl or the heteroaryl being optionally substituted with one or more substituents chosen from a halogen and $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkoxy, $C_3$-$C_7$-cycloalkyl-$C_1$-$C_6$-alkylene-O—, $C_1$-$C_6$-fluoroalkoxy, nitro or cyano groups;

the nitrogen atom(s) of A being optionally substituted with $R_6$ when the nitrogen is adjacent to a carbon atom substituted with an oxo group, or with $R_7$ in the other cases;

$R_6$ represents a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl, aryl-$C_1$-$C_5$-alkylene, heteroaryl or heteroaryl-$C_1$-$C_5$-alkylene group, the aryl or the heteroaryl being optionally substituted with one or more substituents chosen from a halogen and $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkoxy, $C_3$-$C_7$-cycloalkyl-$C_1$-$C_6$-alkylene-O—, $C_1$-$C_6$-fluoroalkoxy, nitro or cyano groups;

$R_7$ represents a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene, $C_1$-$C_6$-alkyl-C(O)—, $C_3$-$C_7$-cycloalkyl-$C_1$-$C_3$-alkylene-(CO)—, $C_1$-$C_6$-fluoroalkyl-C(O)—, $C_3$-$C_7$-cycloalkyl-C(O)—, aryl-C(O)—, aryl-$C_1$-$C_6$-alkylene-C(O)—, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, aryl-S(O)$_2$— or aryl-$C_1$-$C_6$-alkylene-S(O)$_2$— or aryl group.

In the compounds of general formula (I):
the sulfur atom(s) of the heterocycle A may be in oxidized form (S(O) or S(O)$_2$);
the nitrogen atom(s) of the heterocycle A may be in oxidized form (N-oxide);
the nitrogen atom in position 4, 5, 6 or 7 of the pyrrolopyridine may be in oxidized form (N-oxide).

DETAILED DESCRIPTION OF THE INVENTION

In the context of the invention, examples of groups W that may be mentioned include indolinyl, isoindolinyl, indolyl, isoindolyl, benzofuryl, dihydrobenzofuryl, benzothiophenyl, dihydrobenzothiophenyl, benzoxazolyl, dihydrobenzoxazolinyl, isobenzofuryl, dihydroisobenzofuryl, benzimidazolyl, dihydrobenzimidazolyl, indazolyl, benzothiazolyl, isobenzothiazolyl, dihydroisobenzothiazolyl, benzotriazolyl, quinolyl, dihydroquinolyl, tetrahydroquinolyl, isoquinolyl, dihydroisoquinolyl, tetrahydroisoquinolyl, benzoxazinyl, dihydrobenzoxazinyl, benzothiazinyl, dihydrobenzothiazinyl, cinnolinyl, quinazolinyl, dihydroquinazolinyl, tetrahydroquinazolinyl, quinoxalinyl, dihydroquinoxalinyl, tetrahydroquinoxalinyl, phthalazinyl, dihydrophthalazinyl, tetrahydrophthalazinyl, tetrahydrobenz[b]azepinyl, tetrahydrobenz[c]azepinyl, tetrahydrobenz[d]azepinyl, tetrahydrobenzo[b][1,4]diazepinyl, tetrahydrobenzo[e][1,4]diazepinyl, tetrahydrobenzo[b][1,4]oxazepinyl and tetrahydrobenzo[b][1,4]thiazepinyl groups; these groups possibly being substituted as defined in the general formula (I).

In the context of the present invention, the following meanings apply:

$C_t$-$C_z$ in which t and z may take the values from 1 to 7: a carbon-based chain possibly containing from t to z carbon atoms, for example $C_1$-$C_3$ is a carbon-based chain that may contain from 1 to 3 carbon atoms;

an alkyl: a saturated, linear or branched aliphatic group. Examples that may be mentioned include methyl, ethyl, propyl, isopropyl, butyl, isobutyl, tert-butyl, pentyl, etc. groups;

an alkylene: a saturated, linear or branched divalent alkyl group, for example a $C_{1-3}$-alkylene group represents a linear or branched divalent carbon-based chain of 1 to 3 carbon atoms, for example a methylene, ethylene, 1-methylethylene or propylene;

a cycloalkyl: a cyclic carbon-based group. Examples that may be mentioned include cyclopropyl, cyclobutyl, cyclopentyl, cyclohexyl, etc. groups;

a fluoroalkyl: an alkyl group of which one or more hydrogen atoms have been substituted with a fluorine atom;

an alkoxy: a radical —O-alkyl in which the alkyl group is as defined above;

a cycloalkoxy: a radical —O-cycloalkyl in which the cycloalkyl group is as defined above;

a fluoroalkoxy: an alkoxy group of which one or more hydrogen atoms have been substituted with a fluorine atom;

a thioalkyl: a radical —S-alkyl in which the alkyl group is as defined above;

a thiofluoroalkyl: a thioalkyl group of which one or more hydrogen atoms have been substituted with a fluorine atom;

an aryl: a cyclic aromatic group containing between 6 and 10 carbon atoms. Examples of aryl groups that may be mentioned include phenyl and naphthyl groups;

a heteroaryl: an aromatic cyclic group containing 5 to 10 members containing 1 to 4 heteroatoms chosen from O, S or N. For example, the following groups may be mentioned imidazolyl, thiazolyl, oxazolyl, furyl, thiophenyl, oxadiazolyl, tetrazolyl, pyridyl, pyrazinyl, pyrimidinyl, pyridazinyl, indolyl, benzofuryl, benzothiophenyl, benzoxazolyl, benzimidazolyl, indazolyl, benzothiazolyl, isobenzothiazolyl, benzotriazolyl, quinolyl, isoquinolyl, quinoxalinyl cinnolinyl, quinazolinyl, phthalazinyl, naphthyridinyl;

a heterocycle: a saturated, partially unsaturated or aromatic 5- to 7-membered cyclic group comprising from one to three heteroatoms chosen from O, S and N;

a halogen atom: a fluorine, a chlorine, a bromine or an iodine;

"oxo" means "=O";

"thio" means "=S".

The compounds of formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

The compounds of formula (I) may exist in the form of bases or of acid-addition salts. Such addition salts form part of the invention.

These salts are advantageously prepared with pharmaceutically acceptable acids, but the salts of other acids that are useful, for example, for purifying or isolating the compounds of formula (I) also form part of the invention.

The compounds of general formula (I) may be in the form of hydrates or solvates, i.e. in the form of associations or combinations with one or more water molecules or with a solvent. Such hydrates and solvates also form part of the invention.

Among the compounds of general formula (I) that are subjects of the invention, a first subgroup of compounds consists of the compounds for which, if n is equal to 0, then the substituent(s) X, which may be identical or different, are chosen from a halogen atom and $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkoxy, $C_3$-$C_7$-cycloalkyl-$C_1$-$C_3$-alkylene-O—, $C_1$-$C_6$-fluoroalkoxy, cyano, C(O)

$NR_1R_2$, nitro, $NR_1R_2$, $C_1$-$C_6$-thioalkyl, —S(O)—$C_1$-$C_6$-alkyl, —S(O)$_2$—$C_1$-$C_6$-alkyl, $SO_2NR_1R_2$, $NR_3COR_4$ or $NR_3SO_2R_5$ groups.

Among the compounds of general formula (I) that are subjects of the invention, a second subgroup of compounds consists of the compounds for which n is equal to 0 or 1.

Among the compounds of general formula (I) that are subjects of the invention, a third subgroup of compounds consists of the compounds for which the pyrrolopyridine nucleus is a pyrrolo[3,2-b]pyridine group, a pyrrolo[3,2-c]pyridine group, a pyrrolo[2,3-c]pyridine group or a pyrrolo[2,3-b]pyridine group; the pyrrolopyridine nucleus being optionally substituted in carbon position 4, 5, 6 and/or 7 with one or more substituents X, which may be identical or different, chosen from a halogen atom and $C_1$-$C_6$-alkyl or $C_1$-$C_6$-fluoroalkyl groups.

Among the compounds of general formula (I) that are subjects of the invention, a fourth subgroup of compounds consists of the compounds for which the pyrrolopyridine nucleus is a pyrrolo[3,2-b]pyridine group, a pyrrolo[3,2-c]pyridine group, a pyrrolo[2,3-c]pyridine group or a pyrrolo[2,3-b]pyridine group; the pyrrolopyridine nucleus being optionally substituted in carbon position 5 with a substituent X as defined in the general formula (I).

Among the compounds of general formula (I) that are subjects of the invention, a fifth subgroup of compounds consists of the compounds for which the pyrrolopyridine nucleus is a pyrrolo[2,3-b]pyridine group optionally substituted in carbon position 4, 5, 6 and/or 7 with one or more substituents X, which may be identical or different, chosen from a halogen atom, more particularly fluorine, and a $C_1$-$C_6$-fluoroalkyl group, more particularly a trifluoromethyl.

Among the compounds of the fifth subgroup, a sixth subgroup of compounds consists of the compounds for which the pyrrolopyridine nucleus is a pyrrolo[2,3-b]pyridine group optionally substituted in carbon position 5 with a substituent X chosen from a halogen atom, more particularly fluorine, and a $C_1$-$C_6$-fluoroalkyl group, more particularly a trifluoromethyl.

Among the compounds of general formula (I) that are subjects of the invention, a seventh subgroup of compounds consists of the compounds for which
Y represents a group chosen from imidazolyl, thiazolyl, oxazolyl, furyl, thiophenyl, oxadiazolyl, tetrazolyl, pyridyl, pyrazinyl, pyrimidinyl, pyridazinyl, indolyl, benzofuryl, benzothiophenyl, benzoxazolyl, benzimidazolyl, indazolyl, benzothiazolyl, isobenzothiazolyl, benzotriazolyl, quinolyl, isoquinolyl, quinoxalinyl, cinnolinyl, quinazolinyl, phthalazinyl and naphthyridinyl groups; this group being optionally substituted as defined in the general formula (I).

Among the compounds of the seventh subgroup, an eighth subgroup of compounds consists of the compounds for which Y represents a pyridyl.

Among the compounds of general formula (I) that are subjects of the invention, a ninth subgroup of compounds consists of the compounds for which
W is chosen from indolinyl, isoindolinyl, indolyl, isoindolyl, benzofuryl, dihydrobenzofuryl, benzothiophenyl, dihydrobenzothiophenyl, benzoxazolyl, dihydrobenzoxazolinyl, isobenzofuryl, dihydroisobenzofuryl, benzimidazolyl, dihydrobenzimidazolyl, indazolyl, benzothiazolyl, isobenzothiazolyl, dihydroisobenzothiazolyl, benzotriazolyl, quinolyl, dihydroquinolyl, tetrahydroquinolyl, isoquinolyl, dihydroisoquinolyl, tetrahydroisoquinolyl, benzoxazinyl, dihydrobenzoxazinyl, benzothiazinyl, dihydrobenzothiazinyl, cinnolinyl, quinazolinyl, dihydroquinazolinyl, tetrahydroquinazolinyl, quinoxalinyl, dihydroquinoxalinyl, tetrahydroquinoxalinyl, phthalazinyl, dihydrophthalazinyl, tetrahydrophthalazinyl, tetrahydrobenz[b]azepinyl, tetrahydrobenz[c]azepinyl, tetrahydrobenz[d]azepinyl, tetrahydrobenzo[b][1,4]diazepinyl, tetrahydrobenzo[e][1,4]-diazepinyl, tetrahydrobenzo[b][1,4]oxazepinyl and tetrahydrobenzo[b][1,4]thiazepinyl groups; these groups possibly being optionally substituted as defined in the general formula (I).

Among the compounds of general formula (I) that are subjects of the invention, a tenth subgroup of compounds consists of the compounds for which
W represents a benzimidazolyl or benzothiazolyl group,
the carbon atom(s) of W being optionally substituted with one or more $C_1$-$C_6$-alkyl groups, more particularly methyl;
the nitrogen atom(s) of W being optionally substituted with a $C_1$-$C_6$-alkyl group, more particularly methyl.

The compounds for which n, X, Y and W are all as defined in the subgroups of compounds of general formula (I) above form an eleventh subgroup.

In the text hereinbelow, the term "leaving group" means a group that can be readily cleaved from a molecule by breaking a heterolytic bond, with loss of an electron pair. This group may thus be readily replaced with another group, for example during a substitution reaction. Such leaving groups are, for example, halogens or an activated hydroxyl group such as a methanesulfonate, benzenesulfonate, p-toluenesulfonate, triflate, acetate, etc. Examples of leaving groups and references for preparing them are given in "Advances in Organic Chemistry", J. March, $5^{th}$ Edition, Wiley Interscience, 2001.

In accordance with the invention, the compounds of general formula (I) may be prepared according to the process illustrated in scheme 1 below.

According to scheme 1, the compounds of general formula (IV) may be obtained by reacting a compound of general formula (II) in which X is as defined in the general formula (I) above and B represents a $C_1$-$C_6$-alkoxy or hydroxyl group, with a compound of general formula (III), in which y and n are as defined in the general formula (I) above and R' represents a leaving group or a hydroxyl group.

When the compound of general formula (III) is defined such that n is equal to 1, 2 or 3 and R' represents a leaving group such as a bromine or iodine atom, the reaction may be performed in the presence of a base such as sodium hydride or potassium carbonate, in a polar solvent such as dimethylformamide, dimethyl sulfoxide or acetone (n=1: Kolasa T., Bioorg. Med. Chem. 1997, 5 (3) 507, n=2: Abramovitch R., Synth. Commun., 1995, 25 (1), 1).

Scheme 1

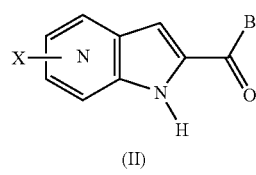

(II)

B = OH or $C_1$-$C_6$-alkoxy

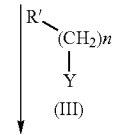

(III)

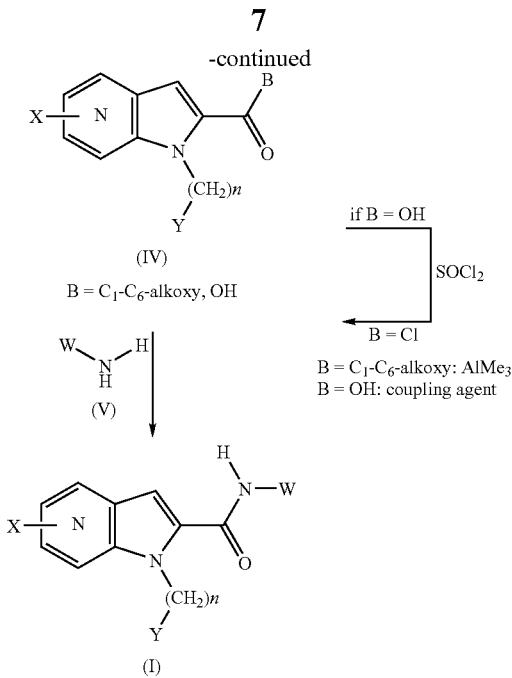

When the compound of general formula (III) is defined such that n is equal to 0 and R' represents a leaving group such as a bromine, chlorine or iodine atom, the reaction may be performed by application and adaptation of the methods described by S. L. Buchwald et al. (*J. Am. Chem. Soc.*, 2001, 123, 7727 and 2002, 124, 11684), preferably under an inert atmosphere in basic medium, for example in the presence of potassium triphosphate, in the presence of a copper salt such as copper iodide, optionally in the presence of an additive such as N,N'-dimethylcyclohexane-1,2-diamine, the whole in an organic solvent such as toluene.

When the compound of general formula (III) is defined such that n is equal to 1, 2 or 3 and R' represents a hydroxyl group, the compounds of general formula (IV) may be obtained by reacting the compound of general formula (II) with a compound of general formula (III) in the presence of a phosphine such as triphenylphosphine and a reagent such as diethyl azodicarboxylate in solution in a solvent such as dichloromethane or tetrahydrofuran (O. Mitsunobu, *Synthesis*, 1981, 1-28).

In the context of the invention, the compounds of general formula (IV) in which B represents a $C_1$-$C_6$-alkoxy group may be converted into compounds of general formula (IV) in which B represents a hydroxyl group according to methods known to those skilled in the art, for example in the presence of a base such as sodium hydroxide in a solvent such as methanol or ethanol, at a temperature of between 20° C. and the boiling point of the reaction medium.

In the context of the invention, the compounds of general formula (IV) in which B represents a hydroxyl group may be converted into compounds of general formula (IV) in which B represents a $C_1$-$C_6$-alkoxy group according to methods known to those skilled in the art, for example in the presence of an acid such as sulfuric acid in a solvent such as methanol or ethanol.

In the case of the compounds of general formula (IV), in which B represents a $C_1$-$C_6$-alkoxy group, the compound of general formula (I) can be obtained by reacting a compound of general formula (IV), as obtained above, with an amide of the compound of general formula (V), in which W is as defined in general formula (I) above, at the reflux point of a solvent such as toluene. The aluminum amide of the compound of general formula (V) is prepared by first reacting trimethylaluminum with the amines of general formula (V).

In the context of the invention, the compounds of general formula (IV) in which B represents a hydroxyl group can react with the compounds of general formula (V) to give the compounds of general formula (I) in the presence of a coupling agent such as a dialkylcarbodiimide, [(benzotriazol-1-yl)oxy][tris(pyrrolidino)]phosphonium hexafluorophosphate or diethyl cyanophosphonate, for example, in the presence of a base such as triethylamine, in an inert solvent such as dimethylformamide, or according to the coupling methods of peptide chemistry (M. Bodanszky et al., principles of peptide synthesis, Springer-Verlag, New York, N.Y., 1984, 9-58).

In the case of the compounds of general formula (IV), in which B represents a hydroxyl group, the carboxylic acid function may be converted beforehand into an acid halide such as an acid chloride via the action of thionyl chloride, preferably under an inert atmosphere (for example under nitrogen or under argon) in a solvent such as acetonitrile, dichloromethane, dichloroethane or toluene, at a temperature of between 20° C. and the boiling point of the reaction medium, as described in the literature (for example in WO 2006/059 163). The compound of general formula (I) is then obtained by reacting the compound of general formula (IV), in which B represents a chlorine atom, with the compound of general formula (V), in the presence of a base such as triethylamine or sodium carbonate.

In Scheme 1, the compounds of formulae (II), (III) and (V) and the other reagents, when their mode of preparation is not described, are commercially available, described in the literature or prepared by analogy with numerous processes described in the literature (Merck WO 2006/089 309; P. Roy et al *Synthesis* 2005, 16, 2751-2757; N. Lahance et al., *Synthesis* 2005, 15, 2571-2577; C. Barberis et al., *Tetrahedron Lett* 2005, 46(51), 8877-8880; T. Lomberget *Synlett* 2005, 13, 2080-2082; 1909; M. Nazare et al., *Angew Chem Int Ed* 2004, 43(34), 4526-4528; P. M. Fresneda et al., *Tetrahedron Lett* 2000, 41(24), 4777-4780; M. H. Fisher et al., *J Heterocyclic Chem* 1969, 6, 775; B. Frydman et al., *J Am Chem Soc* 1965, 87, 3530; L. N. Yakhontov *Tetrahedron Lett* 1969, 1909; B. Frydman *J Org Chem* 1968, 33(10), 3762; G. P. Fagan et al., *J Med Chem* 1988 31(5), 944; OSI Pharmaceuticals WO 2004/104 001; WO 03/049 702; U.S. Pat. No. 0,149,367; WO 03/068 749, for example).

The compounds of general formula (II), (IV) or (I), in which X represents an alkyl group, may be obtained via a coupling reaction, catalyzed with a metal such as palladium or iron, performed on the corresponding compounds of general formula (II), (IV) or (I), in which X represents a halogen atom, for example chlorine, in the presence, for example, of an alkylmagnesium halide or an alkylzinc halide according to the methods described in the literature (A. Furstner et al., *J Am Chem Soc* 2002, 124(46), 13856; G. Queguiner et al., *J Org Chem* 1998, 63(9), 2892 for example) or known to those skilled in the art.

The compounds of general formulae (II), (IV) and (I), in which X represents a cyano group or an aryl, may be obtained via a coupling reaction, catalyzed with a metal such as palladium, performed on the corresponding compounds of general formula (II), (IV) or (I), in which X represents, for example, a bromine atom, in the presence of trimethylsilyl cyanide or an arylboronic acid, or via any other method described in the literature or known to those skilled in the art.

The compounds of general formulae (I), (II) and (IV), in which X represents a group $NR_1R_2$, $NR_3COR_4$ or $NR_3SO_2R_5$, may be obtained from the corresponding compounds of general formulae (I), (II) and (IV), in which X represents, for example, a bromine atom, via a coupling reaction with, respectively, an amine, an amide or a sulfonamide in the presence of a base, a phosphine and a palladium-based catalyst, according to methods described in the literature or known to those skilled in the art.

The compounds of general formulae (II), (IV) and (I), in which X represents a group C(O)NR$_1$R$_2$, may be obtained from the corresponding compounds of general formula (II), (IV) or (I), in which X represents a cyano group, according to methods described in the literature or known to those skilled in the art.

The compounds of general formulae (II), (IV) and (I), in which X represents a group —S(O)-alkyl or —S(O)$_2$-alkyl, may be obtained by oxidation of the corresponding compounds of general formula (II), (IV) or (I), in which X represents a $C_1$-$C_6$-thioalkyl group, according to methods described in the literature or known to those skilled in the art.

The compounds of general formulae (II), (IV) and (I), in which X represents a group NR$_1$R$_2$, NR$_3$COR$_4$ or NR$_3$SO$_2$R$_5$, may be obtained from the corresponding compounds of general formula (II), (IV) or (I), in which X represents nitro group, for example via reduction, and then acylation or sulfonylation, according to methods described in the literature or known to those skilled in the art.

The compounds of general formulae (II), (IV) and (I), in which X represents a group SO$_2$NR$_1$R$_2$ may be obtained via a method similar to that described in *Pharmazie* 1990, 45, 346, or according to methods described in the literature or known to those skilled in the art.

The compounds of general formula (I), in which R$_7$ represents a hydrogen atom, may be obtained from compounds of general formula (I) in which, for example, R$_7$ represents a phenylmethyl group, via hydrogenation in the presence of a palladium-based catalyst or via any method described in the literature or known to those skilled in the art.

The examples that follow describe the preparation of certain compounds in accordance with the invention. These examples are not limiting and serve merely to illustrate the present invention. The numbers of the illustrated compounds refer to those given in Table 1. The elemental microanalyses, the LC-MS analyses (liquid chromatography coupled to mass spectrometry), the IR spectra and/or the NMR spectra confirm the structures of the obtained compounds.

EXAMPLE 1

Compound 1

N-(2-methylbenzothiazol-5-yl)-5-fluoro-1-[(4-pyridyl)methyl]-1H-pyrrolo[2,3-b]pyridine-2-carboxamide 1.1 2-amino-3-iodo-5-fluoropyridine 5 g (44.6 mmol) of 2-amino-5-fluoropyridine, 13.9 g (44.6 mmol) of silver sulfate and 400 mL of ethanol are introduced into a 500 mL two-necked flask equipped with a magnetic stirrer. 11.31 g (44.6 mmol) of iodine powder are then added portionwise. Stirring is continued at room temperature for 24 hours. The resulting yellow suspension is filtered, the precipitate is rinsed with ethanol and the filtrate is concentrated under reduced pressure. The residue thus obtained is taken up in a mixture of ethyl acetate (200 mL) and saturated sodium carbonate solution (200 mL). After separation, the organic phase is successively washed with aqueous 25% sodium thiosulfate solution and with saturated aqueous sodium chloride solution and then dried over sodium sulfate and concentrated under reduced pressure. The resulting solid is purified by chromatography on a column of silica, eluting with a mixture of n-heptane and ethyl acetate. 2.67 g of the expected product are obtained.

$^1$H NMR (DMSO D$_6$), δ (ppm): 7.9 (m, 2H); 5.9 (s, 2H).

1.2 5-fluoro-1H-pyrrolo[2,3-b]pyridine-2-carboxylic acid 2 g (7.98 mmol) of 2-amino-3-iodo-5-fluoropyridine, obtained according to the protocol described in step 1.1, 2.1 g (23.95 mmol) of pyruvic acid, 2.68 g (23.95 mmol) of 1,4-diazabicyclo[2.2.2]octane (DABCO) and 50 mL of anhydrous dimethylformamide are introduced into a sealed 100 mL tube equipped with a magnetic stirrer and maintained under an argon sparge. After a few minutes, 0.18 g (0.8 mmol) of palladium acetate is added. The reaction mixture is stirred and maintained under an argon sparge for 20 minutes and then rapidly sealed and maintained at 100° C. for 3 hours. The cooled solution is concentrated under reduced pressure. The residue is then taken up in ethyl acetate (200 mL) and the organic phase is washed three times with 100 mL of water and then extracted with three times 50 mL of aqueous 2N sodium hydroxide solution. The basic aqueous phases are combined, cooled to 0° C. and then acidified by addition of hydrochloric acid (pH 3). The resulting aqueous phase is then extracted with three times 100 mL of ethyl acetate. The combined organic phases are dried over sodium sulfate and then concentrated under reduced pressure. 0.87 g of the expected product is obtained in the form of a yellow powder.

$^1$H NMR (DMSO D$_6$), δ (ppm): 13.2 (s, 1H); 12.4 (s, 1H); 8.4 (dd, 1H); 7.95 (dd, 1H); 7.1 (d, 1H).

1.3 ethyl 5-fluoro-1H-pyrrolo[2,3-b]pyridine-2-carboxylate 0.9 g (5 mmol) of 5-fluoro-1H-pyrrolo[2,3-b]pyridine-2-carboxylic acid, obtained according to the protocol described in step 1.2, and 10 mL of ethanol are introduced into a 100 mL round-bottomed flask equipped with a magnetic stirrer. 0.5 mL of concentrated sulfuric acid is added to the reaction mixture, which is then refluxed for 24 hours. The cooled solution is concentrated under reduced pressure. The residue is taken up in dichloromethane (200 mL) and successively washed with aqueous sodium hydrogen carbonate solution (2×100 mL), with water (50 mL) and then with 50 mL of saturated aqueous sodium chloride solution. The organic phase is dried over sodium sulfate and then concentrated under reduced pressure. 0.87 g of the expected product is isolated.

$^1$H NMR (DMSO D$_6$), δ (ppm): 12.6 (s, 1H); 8.4 (dd, 1H); 8.0 (dd, 1H); 7.1 (d, 1H); 4.3 (q, 2H); 1.3 (t, 3H).

1.4 ethyl 5-fluoro-1-[(4-pyridyl)methyl]-1H-pyrrolo[2,3-b]pyridine-2-carboxylate 0.19 g (1.8 mmol) of 4-pyridylmethanol and then 0.48 g (1.8 mmol) of triphenylphosphine are successively added with stirring to a solution of 0.25 g (1.2 mmol) of ethyl 5-fluoro-1H-pyrrolo[2,3-b]pyridine-2-carboxylate, obtained according to the protocol described in step 1.3, in 10 mL of dry tetrahydrofuran maintained under an inert atmosphere. 0.32 g (1.8 mmol) of diethyl azodicarboxylate is then added dropwise at 0° C. The reaction mixture is then stirred for 72 hours at room temperature and then concentrated under reduced pressure. The resulting oil is purified by chromatography on a column of silica gel, eluting with a mixture of heptane and ethyl acetate. 0.26 g of the expected product is isolated.

$^1$H NMR (DMSO D$_6$), δ (ppm): 8.5 (m, 1H); 8.4 (d, 2H); 8.1 (dd, 1H); 7.4 (s, 1H); 6.95 (d, 2H); 5.9 (s, 2H); 4.3 (q, 2H); 1.2 (t, 3H).

1.5 N-(2-methylbenzothiazol-5-yl)-5-fluoro-1-[(4-pyridyl)methyl]-1H-pyrrolo[2,3-b]pyridine-2-carboxamide (compound 1)

0.19 g (1.15 mmol) of 5-amino-2-methylbenzothiazole and 5 mL of dry toluene are introduced, while sparging with nitrogen, into a 50 mL three-necked flask, cooled to 0° C. and equipped with a magnetic stirrer. 0.72 mL (1.44 mmol) of a 2M solution of trimethylaluminum in toluene is then added slowly to this solution. The reaction mixture obtained is maintained under a nitrogen atmosphere and stirred while allowing the temperature gradually to reach 70° C. A solution of 0.28 g (0.93 mmol) of ethyl 5-fluoro-1-[(4-pyridyl)methyl]-1H-pyrrolo[2,3-b]pyridine-2-carboxylate, obtained according to the protocol described in step 1.4, in 5 mL of dry toluene is then added dropwise over 5 minutes. The reaction mixture is then refluxed for 3 hours. After returning to room temperature, the suspension obtained is cooled to 0° C. and then hydrolyzed by dropwise addition of 20 mL of cold water, followed by addition of 5 mL of 1N hydrochloric acid. After stirring for 30 minutes, the pH of the reaction mixture is adjusted to 8 by adding saturated sodium hydrogen carbonate solution. The resulting mixture is then extracted with ethyl acetate. The combined organic phases are successively washed with saturated aqueous sodium hydrogen carbonate solution, with water and then with saturated sodium chloride solution. After drying over sodium sulfate, filtering and concentrating the filtrate under reduced pressure, an oil is obtained, which gradually crystallizes at rest. The solid thus formed is slurried in a minimum amount of dichloromethane, filtered and then stirred in hot diisopropyl ether to give, after filtration and drying, 0.127 g of the expected product in the form of a beige-colored solid.

Melting point: 217-219° C.

$^1$H NMR (DMSO D$_6$), δ (ppm): 10.7 (s, 1H); 8.45 (m, 3H); 8.3 (d, 1H); 8.2 (dd, 1H); 7.9 (d, 1H); 7.7 (dd, 1H); 7.5 (s, 1H); 7.0 (d, 2H); 5.9 (s, 2H); 2.8 (s, 3H).

EXAMPLE 2

Compound 2

N-(1,2-dimethyl-1H-benzimidazol-5-yl)-5-fluoro-1-[(4-pyridyl)methyl]-1H-pyrrolo[2,3-b]pyridine-2-carboxamide 0.18 g (1.15 mmol) of 5-amino-1,2-dimethyl-1H-benzimidazole and 5 mL of dry toluene are introduced, under a nitrogen sparge, into a 50 mL three-necked flask, cooled to 0° C. and equipped with a magnetic stirrer. 0.72 mL (1.44 mmol) of a 2M solution of trimethylaluminum in toluene is then added slowly to this solution. The reaction mixture obtained is maintained under a nitrogen atmosphere and stirred while allowing the temperature gradually to reach 70° C. A solution of 0.3 g (0.96 mmol) of ethyl 5-fluoro-1-[(4-pyridyl)methyl]-1H-pyrrolo[2,3-b]pyridine-2-carboxylate, obtained according to the protocol described in step 1.4, in 5 mL of dry toluene is then added dropwise over 5 minutes. The reaction mixture is then refluxed for 18 hours. After returning to room temperature, the suspension obtained is cooled to 0° C. and then hydrolyzed by dropwise addition of 20 mL of cold water, followed by addition of 5 mL of 1N hydrochloric acid. After stirring for 30 minutes, the pH of the reaction mixture is adjusted to 8 by adding saturated sodium hydrogen carbonate solution. The resulting mixture is then extracted with ethyl acetate. The combined organic phases are successively washed with saturated aqueous sodium hydrogen carbonate solution, with water and then with saturated NaCl solution. The resulting organic phase is then dried over sodium sulfate and filtered through a sinter funnel. Gradual formation of a white precipitate is observed. This precipitate is collected, rinsed with ethyl acetate and dried under vacuum. 0.157 g of the expected product is obtained in the form of a white solid.

Melting point: 263-265° C.

$^1$H NMR (DMSO D$_6$), δ (ppm): 10.4 (s, 1H); 8.4 (m, 3H); 8.15 (dd, 1H); 7.9 (m, 1H); 7.45 (m, 3H); 7.0 (d, 2H); 5.9 (s, 2H); 3.7 (s, 3H); 2.5 (s, 3H).

EXAMPLE 3

Compound 3

N-(1,2-dimethyl-1H-benzimidazol-5-yl)-1-[(4-pyridyl)methyl]-1H-pyrrolo[2,3-b]pyridine-2-carboxamide

3.1 2-(t-butyloxycarbonylamino)-3-methylpyridine 31 g (142.03 mmol) of di-tert-butyl dicarbonate and 35 mL of hexane are introduced into a 100 mL three-necked flask equipped with a magnetic stirrer, and the solution is brought to reflux. A solution of 10 g (88.77 mmol) of 2-amino-3-methylpyridine in 10 mL of ethyl acetate is then added dropwise over a period of 2 hours. Refluxing is continued for 1 hour after the end of the addition. After returning to room temperature, 20 mL of hexane are added and the white precipitate formed after stirring the reaction mixture is collected by filtration, rinsed with hexane and dried under reduced pressure. 15.5 g of white crystals are obtained.

$^1$H NMR (CDCl$_3$), δ (ppm): 8.3 (dd, 1H); 7.5 (dd, 1H); 7.4 (s, 1H); 7.1 (ddd, 1H); 2.3 (s, 3H); 1.5 (s, 9H).

3.2 ethyl 1H-pyrrolo[2,3-b]pyridine-2-carboxylate 5 g (24.01 mmol) of 2-(t-butyloxycarbonylamino)-3-methylpyridine, obtained according to the protocol described in step 3.1, and 50 mL of dry tetrahydrofuran are introduced into a 250 mL three-necked flask equipped with a magnetic stirrer and maintained under a nitrogen atmosphere. 30 mL (48.02 mmol) of a 1.6 M solution of n-butyllithium in THF are then added dropwise, while keeping the temperature below 5° C. After stirring for 1 hour at 0° C., the lithiated derivative thus obtained is added to a solution of 7.08 g (48.02 mmol) of diethyl oxalate in 50 mL of dry tetrahydrofuran maintained at a temperature of −3° C. The reaction medium is then allowed to return to room temperature, and is then poured onto a solution of 25 mL of 6N hydrochloric acid cooled to 0° C., while keeping the temperature below 10° C. The mixture obtained is then stirred at 50° C. for 2 hours and then at room temperature overnight. The reaction medium is adjusted to pH 3 with sodium hydroxide and is extracted with diethyl ether. The organic phase is dried over sodium sulfate, filtered and concentrated under reduced pressure. 1.8 g of product, used without further purification in the following steps, are obtained.

¹H NMR (CDCl₃), δ (ppm): 8.8 (dd, 1H); 8.15 (dd, 1H); 7.2 (m, 2H); 4.5 (q, 2H); 1.5 (t, 3H).

3.3 ethyl 1-[(4-pyridyl)methyl]-1H-pyrrolo[2,3-b]pyridine-2-carboxylate 0.51 g (4.73 mmol) of 4-pyridylmethanol and then 1.24 g (4.73 mmol) of triphenyl-phosphine are successively added with stirring to a solution of 0.6 g (3.15 mmol) of ethyl 1H-pyrrolo[2,3-b]pyridine-2-carboxylate, obtained according to the protocol described in step 3.2, in 40 mL of dry tetrahydrofuran, maintained under an inert atmosphere. 0.82 g (4.73 mmol) of diethyl azodicarboxylate is then added dropwise at 0° C. The reaction mixture is stirred for 24 hours at room temperature and then concentrated under reduced pressure. A mixture of water and ethyl acetate (20 mL, v/v) is added and the pH of the reaction mixture is adjusted to 5-6 by adding acetic acid. The organic phase separated out is then washed twice with 10 mL of water and once with 10 mL of saturated sodium chloride solution and then dried over magnesium sulfate. After concentrating under reduced pressure, the resulting oil is purified by chromatography on a column of silica gel. 0.66 g of expected product is isolated.

¹H NMR (CDCl₃), δ (ppm): 8.5 (m, 3H); 8.1 (dd, 1H); 7.35 (s, 1H); 7.2 (m, 1H); 7.0 (d, 2H); 6.0 (s, 2H); 4.3 (q, 2H); 1.3 (t, 3H).

3.4 N-(1,2-Dimethyl-1H-benzimidazol-5-yl)-1-[(4-pyridyl)methyl]-1H-pyrrolo[2,3-b]pyridine-2-carboxamide (compound 3)

0.189 g (1.17 mmol) of 5-amino-1,2-dimethyl-1H-benzimidazole and 10.6 mL of toluene are introduced, under an argon sparge, into a 50 mL Keller flask equipped with a magnetic stirrer. 0.85 mL (1.71 mmol) of a 2M solution of trimethylaluminum in toluene is then added dropwise at room temperature. The reaction mixture is maintained at 50° C. for 30 minutes, and 0.3 g (1.07 mmol) of ethyl 1-[(4-pyridyl)methyl]-1H-pyrrolo[2,3-b]pyridine-2-carboxylate, obtained according to the protocol described in step 3.3, is then added. The reaction mixture is then refluxed for 5 hours. After returning to room temperature, the mixture is poured into normal sodium hydroxide and extracted three times with 10 mL of ethyl acetate. The combined organic phases are successively washed with 10 mL of water and with 10 mL of saturated aqueous sodium chloride solution, dried over sodium sulfate and then concentrated under reduced pressure. The resulting solid is purified by chromatography on a column of silica, eluting with a mixture of dichloromethane and methanol. The isolated solid is then recrystallized from isopropanol. 0.2 g of the expected product is obtained.

Melting point: 236-246° C.

¹H NMR (DMSO D₆), δ (ppm): 8.4 (m, 3H); 8.2 (dd, 1H); 7.85 (d, 1H); 7.4 (m, 3H) 7.2 (dd, 1H); 7.0 (d, 2H); 5.9 (s, 2H); 3.7 (s, 3H); 2.5 (s, 3H).

EXAMPLE 4

Compound 4

N-(2-methylbenzothiazol-5-yl)-1-[(4-pyridyl)methyl]-1H-pyrrolo[2,3-b]pyridine-2-carboxamide 0.224 g (1.37 mmol) of 5-amino-2-methylbenzothiazole and 12.44 mL of toluene are introduced, under an argon sparge, into a 50 mL Keller flask equipped with a magnetic stirrer. 1 mL (1.99 mmol) of a 2M solution of trimethylaluminum in toluene is then added dropwise at room temperature. The reaction mixture is maintained at 50° C. for 30 minutes, and a solution of 0.35 g (1.24 mmol) of ethyl 1-[(4-pyridyl)methyl]-1H-pyrrolo[2,3-b]pyridine-2-carboxylate obtained according to the protocol described in step 3.3, in 12.44 mL of dry toluene is then added dropwise over 5 minutes. The reaction mixture is then refluxed for 14 hours. After cooling to room temperature, 1 mL (1.99 mmol) of a 2M solution of trimethylaluminum in toluene is added to the reaction medium and the reaction mixture is again refluxed for 7 hours. After returning to room temperature, the mixture is poured into normal sodium hydroxide and extracted three times with 10 mL of ethyl acetate. The combined organic phases are successively washed with 10 mL of water and with 10 mL of saturated aqueous sodium chloride solution, dried over sodium sulfate and then concentrated under reduced pressure. The resulting solid is purified by chromatography on a column of silica, eluting with a mixture of dichloromethane and ethyl acetate. The isolated solid is then recrystallized from isopropanol. 0.276 g of the expected product is obtained.

Melting point: 211-236° C.

¹H NMR (DMSO D₆), δ (ppm): 8.5 (m, 3H); 8.1 (m, 3H); 7.8 (d, 1H); 7.7 (dd, 1H); 7.25 (3, 3H); 7.1 (s, 1H); 6.1 (s, 2H); 2.8 (s, 3H).

EXAMPLE 5

Compound 5

N-(2-methylbenzothiazol-5-yl)-5-trifluoromethyl-1-[(4-pyridyl)methyl]-1H-pyrrolo[2,3-b]pyridine-2-carboxamide

5.1 2-amino-3-iodo-5-trifluoromethylpyridine 2 g (12.34 mmol) of 2-amino-5-trifluoromethylpyridine, 3.85 g (12.34 mmol) of silver sulfate and 80 mL of ethanol are introduced into a 500 mL two-necked flask equipped with a magnetic stirrer. 3.13 g (12.34 mmol) of iodine powder are then added portionwise to the reaction medium stirred at room temperature. The reaction mixture is then stirred at room temperature for 48 hours. The resulting yellow suspension is filtered, the precipitate is rinsed with ethanol and the filtrate is evaporated under reduced pressure. The residue is taken up in 100 mL of dichloromethane. This solution is washed successively with 20 mL of aqueous 5% sodium hydroxide solution, 20 mL of water and 20 mL of saturated aqueous sodium chloride solution and then dried over sodium sulfate and concentrated under reduced pressure. The resulting solid is purified by chromatography on a column of silica, eluting with a mixture of n-heptane and ethyl acetate. 1.71 g of product are obtained in the form of a pink powder.

¹H NMR (DMSO D₆), δ (ppm): 8.3 (s, 1H); 8.1 (s, 1H); 6.8 (s, 2H).

5.2 5-trifluoromethyl-1H-pyrrolo[2,3-b]pyridine-2-carboxylic acid 2 g (6.94 mmol) of 2-amino-3-iodo-5-trifluoromethylpyridine, obtained according to the protocol described in step 5.1, 1.89 g (20.83 mmol) of pyruvic acid, 2.41 g (20.83 mmol) of 1,4-diazabicyclo[2.2.2]octane (DABCO) and 20 mL of anhydrous dimethylformamide are introduced into a sealed 25 mL tube, equipped with a magnetic stirrer and maintained under an argon sparge. After a few minutes, 0.78 g (3.47 mmol) of palladium acetate is added. The reaction mixture is stirred under an argon sparge for 20 minutes and then rapidly sealed and maintained at 110° C. for 3 hours. The cooled solution is concentrated under reduced pressure. The residue is taken up in ethyl acetate and water. After separation of the phases by settling, the organic phase is extracted with twice 50 mL of aqueous 2N sodium hydroxide solution. The basic aqueous phases are combined, cooled to 0° C. and then acidified by adding hydrochloric acid (pH 3). The aqueous phase is extracted with ethyl acetate (4×50 mL) and the combined organic phases are dried over sodium sulfate and then concentrated under reduced pressure. 0.97 g of expected product is obtained in the form of a yellow powder, which is used without further purification in the following steps.

$^1$H NMR (DMSO D$_6$), δ (ppm): 12.8 (s, 1H); 8.7 (d, 1H); 8.5 (d, 1H); 7.2 (s, 1H).

5.3 ethyl 5-trifluoromethyl-1H-pyrrolo[2,3-b]pyridine-2-carboxylate 0.9 g (3.91 mmol) of 5-trifluoromethyl-1H-pyrrolo[2,3-b]pyridine-2-carboxylic acid, obtained according to the protocol described in step 5.2, and 10 mL of ethanol are introduced into a 25 mL round-bottomed flask equipped with a magnetic stirrer. 0.5 mL of concentrated sulfuric acid is added to this solution. The reaction mixture is then refluxed for 20 hours. The cooled solution is concentrated under reduced pressure. The residue is taken up in dichloromethane (50 mL) and the organic phase is successively washed with three times 20 mL of saturated aqueous sodium hydrogen carbonate solution, with 20 mL of water and then with 20 mL of saturated aqueous sodium chloride solution. The resulting organic phase is dried over sodium sulfate and then concentrated under reduced pressure. 0.85 g of the expected product is isolated in the form of a yellow powder.

$^1$H NMR (DMSO D$_6$), δ (ppm): 13.1 (s, 1H); 8.8 (s, 1H); 8.6 (s, 1H); 7.3 (s, 1H); 4.4 (q, 2H); 1.35 (t, 3H).

5.4 ethyl 5-trifluoromethyl-1-[(4-pyridyl)methyl]-1H-pyrrolo[2,3-b]pyridine-2-carboxylate 0.63 g (5.81 mmol) of 4-pyridylmethanol and then 1.52 g (5.81 mmol) of triphenyl-phosphine are successively added, with stirring, to a solution of 1 g (3.87 mmol) of the product obtained according to the protocol described in step 5.3, in 20 mL of dry tetrahydrofuran, maintained under an inert atmosphere. 1.01 g (5.81 mmol) of diethyl azodicarboxylate are then added dropwise. The reaction mixture is then stirred for 20 hours at room temperature, and then concentrated under reduced pressure. The resulting oil is purified by chromatography on a column of silica gel, eluting with a mixture of heptane and ethyl acetate. 1.23 g of the expected product are isolated in the form of a white solid.

$^1$H NMR (DMSO D$_6$), δ (ppm): 8.8 (d, 1H); 8.7 (d, 1H); 8.45 (d, 2H); 7.55 (s, 1H); 6.95 (d, 2H); 5.9 (s, 2H); 4.3 (q, 2H); 1.2 (t, 3H).

5.5 N-(2-methylbenzothiazol-5-yl)-5-trifluoromethyl-1-[(4-pyridyl)methyl]-1H-pyrrolo[2,3-b]pyridine-2-carboxamide (compound 5)

0.21 g (1.31 mmol) of 5-amino-2-methylbenzothiazole and 5 mL of dry toluene are introduced, under a nitrogen sparge, into a 100 mL three-necked flask, cooled to 0° C. and equipped with a magnetic stirrer. 0.82 mL (1.63 mmol) of a 2M solution of trimethylaluminum in toluene is then added slowly to this solution. The reaction mixture obtained is maintained under a nitrogen atmosphere and stirred while allowing the temperature gradually to reach 70° C. At this temperature, a solution of 0.4 g (1.09 mmol) of ethyl 5-trifluoromethyl-1-[(4-pyridyl)methyl]-1H-pyrrolo[2,3-b]pyridine-2-carboxylate, obtained according to the protocol described in step 5.4, in 15 mL of dry toluene is added dropwise over 5 minutes. The reaction mixture is then refluxed for 5 hours. 20 mL of cold water and 10 mL of 1N hydrochloric acid are then added to the solution cooled to 0° C. After stirring for 30 minutes, the pH of the reaction mixture is adjusted to 8 by adding saturated sodium hydrogen carbonate solution. This mixture is then extracted with three times 50 mL of ethyl acetate. The combined organic phases are successively washed with 20 mL of saturated aqueous sodium hydrogen carbonate solution, 20 mL of water and then with 20 mL of saturated sodium chloride solution. After drying over sodium sulfate, filtering and concentrating the organic filtrate under reduced pressure, the yellow solid obtained is purified by successive chromatographies on a column of silica gel. 0.14 g of expected product is isolated in the form of a white solid.

Melting point: 208-210° C.

$^1$H NMR (DMSO D$_6$), δ (ppm): 10.8 (s, 1H); 8.8 (d, 2H); 8.45 (d, 2H); 8.3 (s, 1H); 7.95 (d, 1H); 7.7 (d, 1H); 7.65 (s, 1H); 7.0 (d, 2H); 6.0 (s, 2H); 2.8 (s, 3H).

EXAMPLE 6

Compound 6

N-(2-methylbenzothiazol-5-yl)-1-(4-pyridyl)-1H-pyrrolo[2,3-b]pyridine-2-carboxamide

6.1 ethyl 1-(4-pyridyl)-1H-pyrrolo[2,3-b]pyridine-2-carboxylate 0.2 g (1.05 mmol) of ethyl 1H-pyrrolo[2,3-b]pyridine-2-carboxylate, obtained according to the protocol described in step 3.2, 0.244 g (1.16 mmol) of 4-iodopyridine, 0.01 g (0.05 mmol) of copper iodide, 0.47 g (2.21 mmol) of tripotassium phosphate, 0.029 g (0.21 mmol) of racemic trans-N,N'-dimethylcyclohexane-1,2-diamine and 2 mL of toluene are introduced into a sealed 25 mL tube, equipped with a magnetic stirrer and maintained under an argon sparge. The reaction mixture is stirred under an argon sparge for 20 minutes and then rapidly sealed and maintained at 130° C. for 5 days. The cooled suspension is diluted in 10 mL of ethyl acetate and 20 mL of water. The aqueous phase is then extracted with twice 30 mL of ethyl acetate. The combined organic phases are successively washed with 10 mL of saturated aqueous sodium hydrogen carbonate solution, 10 mL of water and 10 mL of saturated aqueous sodium chloride solution. The resulting organic phase is then dried over sodium sulfate, filtered and concentrated under reduced pressure. 0.26 g of expected product is isolated in the form of a brown powder.

$^1$H NMR (DMSO D$_6$), δ (ppm): 8.75 (d, 2H); 8.4 (m, 1H); 8.25 (m, 1H); 7.5 (m, 3H); 7.3 (m, 1H); 4.2 (q, 2H); 1.2 (t, 3H).

6.2 N-(2-Methylbenzothiazol-5-yl)-1-(4-pyridyl)-1H-pyrrolo[2,3-b]pyridine-2-carboxamide 0.147 g (0.9 mmol) of 5-amino-2-methylbenzothiazole and 5 mL of toluene are introduced, under an argon sparge, into a 25 mL Keller flask equipped with a magnetic stirrer. 0.56 mL (1.12 mmol) of a 2M solution of trimethylaluminum in toluene is then added dropwise at 0° C. The reaction mixture is maintained at 70° C. for 20 minutes, and 0.2 g (0.75 mmol) of ethyl 1-(4-pyridyl)-1H-pyrrolo[2,3-b]pyridine-2-carboxylate, obtained according to the protocol described in step 6.1, is then added. The reaction mixture is then refluxed for 8 hours, and then left at room temperature over the weekend. 10 mL of cold water and 5 mL of 1N hydrochloric acid are then added to the solution cooled to 0° C. After stirring for 30 minutes, the pH of the reaction mixture is adjusted to 8 by adding saturated sodium hydrogen carbonate solution. This mixture is then extracted with three times 20 mL of ethyl acetate. The combined organic phases are successively washed with 20 mL of saturated aqueous sodium hydrogen carbonate solution, 20 mL of water and then with 20 mL of saturated sodium chloride solution. After drying over sodium sulfate, filtering and concentrating the organic filtrate under reduced pressure, the orange solid obtained is purified by successive chromatographies on a column of silica gel. The isolated solid is then washed with boiling isopropyl ether, and then dried under reduced pressure. 0.217 g of expected product is isolated in the form of an orange solid.

Melting point: 236-238° C.

$^1$H NMR (DMSO D$_6$), δ (ppm): 10.9 (s, 1H); 8.7 (d, 2H); 8.4 (m, 1H); 8.3 (m, 2H); 7.95 (d, 1H); 7.7 (dd, 1H); 7.55 (s, 1H); 7.5 (m, 2H); 7.3 (m, 1H); 2.8 (s, 3H).

EXAMPLE 7

Compound 7

N-(2-methylbenzothiazol-5-yl)-1-(3-pyridyl)-1H-pyrrolo[2,3-b]pyridine-2-carboxamide 7.1 ethyl 1-(3-pyridyl)-1H-pyrrolo[2,3-b]pyridine-2-carboxylate This compound was prepared according to the experimental protocol described in Example 6.1, starting with ethyl 1H-pyrrolo[2,3-b]pyridine-2-carboxylate obtained according to the protocol described in step 3.2 and 3-iodopyridine. A yellow solid is obtained.

$^1$H NMR (DMSO D$_6$), δ (ppm): 8.65 (m, 2H); 8.4 (m, 1H); 8.25 (dd, 1H); 7.9 (m, 1H); 7.55 (m, 1H); 7.5 (s, 1H); 7.3 (m, 1H); 4.2 (q, 2H); 1.2 (t, 3H).

7.2 N-(2-methylbenzothiazol-5-yl)-1-(3-pyridyl)-1H-pyrrolo[2,3-b]pyridine-2-carboxamide (compound 7)

This compound was prepared according to the experimental protocol described in Example 6.2, starting with ethyl 1-(3-pyridyl)-1H-pyrrolo[2,3-b]pyridine-2-carboxylate obtained according to the protocol described in step 7.1 and 5-amino-2-methylbenzothiazole. A yellow solid is obtained.

Melting point: 246-248° C.

$^1$H NMR (DMSO D$_6$), δ (ppm): 11.2 (s, 1H); 8.7 (d, 1H); 8.6 (d, 1H); 8.4 (m, 1H); 8.3 (m, 2H); 7.9 (m, 2H); 7.7 (m, 1H); 7.55 (m, 2H); 7.3 (dd, 1H); 2.8 (s, 3H).

EXAMPLE 8

Compound 8

N-(2-methylbenzothiazol-5-yl)-1-(2-pyridyl)-1H-pyrrolo[2,3-b]pyridine-2-carboxamide 8.1 ethyl 1-(2-pyridyl)-1H-pyrrolo[2,3-b]pyridine-2-carboxylate This compound was prepared according to the experimental protocol described in Example 6.1, starting with ethyl 1H-pyrrolo[2,3-b]pyridine-2-carboxylate obtained according to the protocol described in step 3.2 and 2-iodopyridine. A beige-colored solid is obtained.

$^1$H NMR (DMSO D$_6$), δ (ppm): 8.55 (m, 1H); 8.4 (dd, 1H); 8.2 (dd, 1H); 8.1 (td, 1H); 7.8 (d, 1H); 7.5 (ddd, 1H); 7.4 (s, 1H); 7.3 (dd, 1H); 4.15 (q, 2H); 1.05 (s, 3H).

8.2 N-(2-methylbenzothiazol-5-yl)-1-(2-pyridyl)-1H-pyrrolo[2,3-b]pyridine-2-carboxamide (compound 8)

This compound was prepared according to the experimental protocol described in Example 6.2, starting with ethyl 1-(2-pyridyl)-1H-pyrrolo[2,3-b]pyridine-2-carboxylate obtained according to the protocol described in step 8.1 and 5-amino-2-methylbenzothiazole. A white solid is obtained.

Melting point: 112-114° C.

$^1$H NMR (DMSO D$_6$), δ (ppm): 10.8 (s, 1H); 8.4 (m, 2H); 8.25 (m, 2H); 8.05 (m, 1H) 7.95 (m, 2H); 7.65 (dd, 1H); 7.35 (m, 3H); 2.8 (s, 3H).

Table 1 below illustrates the chemical structures and the physical properties of a number of compounds of general formula (I) according to the invention in which the pyrrolopyridine nucleus is an optionally substituted pyrrolo[2,3-b]pyridine.

In this table:

the "m.p." column gives the melting points of the products in degrees Celsius (° C.);

TABLE 1

(I)

| No. | X | n | Y | W | m.p. (° C.) |
|---|---|---|---|---|---|
| 1 | 5-F | 1 | 4-pyridyl- | 2-methylbenzothiazol-5-yl | 217-219 |
| 2 | 5-F | 1 | 4-pyridyl- | 1,2-dimethylbenzimidazol-5-yl | 263-265 |
| 3 | H | 1 | 4-pyridyl- | 1,2-dimethylbenzimidazol-5-yl | 236-246 |
| 4 | H | 1 | 4-pyridyl- | 2-methylbenzothiazol-5-yl | 211-236 |
| 5 | 5-CF$_3$ | 1 | 4-pyridyl- | 2-methylbenzothiazol-5-yl | 208-210 |
| 6 | H | 0 | 4-pyridyl- | 2-methylbenzothiazol-5-yl | 236-238 |
| 7 | H | 0 | 3-pyridyl- | 2-methylbenzothiazol-5-yl | 246-248 |
| 8 | H | 0 | 2-pyridyl- | 2-methylbenzothiazol-5-yl | 112-114 |

The compounds of the invention were subjected to in vitro and in vivo pharmacological tests that demonstrated their value as substances with therapeutic activities.

Test of Inhibition of the Current Induced with Capsaicin on Rat DRGs

Primary Culture of Rat Dorsal Root Ganglion (DRG) Cells:

The neurons of the DRG naturally express the TRPV1 receptor.

The primary cultures of newborn rat DRGs are prepared using 1-day-old rats. Briefly, after dissection, the ganglions are trypsinized and the cells dissociated by mechanical trituration. The cells are resuspended in an Eagle basal culture medium containing 10% fetal calf serum, 25 mM KCl, 2 mM glutamine, 100 μg/ml gentamicin and 50 ng/ml of NGF, and then deposited on glass slides coated with laminin (0.25×10$^6$ cells per slide), which are then placed in Corning 12-well dishes. The cells are incubated at 37° C. in a humidified atmosphere containing 5% $CO_2$ and 95% air. Cytosine β-D-arabinoside (1 μM) is added 48 hours after culturing, to prevent the growth of non-neuronal cells. The slides are transferred into experimental chambers for the patch-clamp studies after 7-10 days of culturing.

Electrophysiology:

The measuring chambers (volume 800 μl) containing the cell preparation are placed on the platform of an inverted microscope (Olympus IMT2) equipped with Hoffman optics (Modulation Contrast, New York) and observed at a magnification of 400×. The chambers are continuously gravity-infused (2.5 ml/min) using a solution distributor accepting 8 inlets and whose sole outlet, consisting of a polyethylene tube (aperture 500 μm), is placed less than 3 mm from the cell under study. The "whole cell" configuration of the patch-clamp technique was used. The borosilicate glass pipettes (resistance 5-10 MOhms) are brought to the cell by means of a 3D piezoelectric micromanipulator (Burleigh, PC1000). The overall currents (membrane potential set at −60 mV) are recorded with an Axopatch 1D amplifier (Axon Instruments, Foster city, Calif.), connected to a PC running the Pclamp8 software (Axon Instrument). The current plots are recorded on paper and simultaneously digitized (sampling frequency 15 to 25 Hz) and acquired on the hard drive of the PC.

The application of a 1 μM capsaicin solution induces on the DRG cells (voltage set at −70 mV) an entering cationic current. In order to minimize the desensitization of the receptors, a minimum interval of one minute between two applications of capsaicin is observed. After a control period (stabilization of the capsaicin response alone), the test compounds are applied alone at a given concentration (concentration of 10 nM or 1 nM) for a time of 4 to 5 minutes, during which several capsaicin+compound tests are performed (to obtain the maximum inhibition). The results are expressed as a percentage of inhibition of the control capsaicin response.

The percentages of inhibition of the capsaicin response (1 μM) are between 20% and 100% for the most active compounds of the invention tested at concentrations of 0.1 to 10 nM (see the example in Table 2).

TABLE 2

| Compound No. | % inhibition in DRG patch |
|---|---|
| Compound 1 | 50% (10 nM) |

The compounds of the invention are thus efficient in vitro antagonists of receptors of TRPV1 type.

The compounds of the invention may thus be used for the preparation of medicaments, especially for the preparation of a medicament for preventing or treating pathologies in which the TRPV1 receptors are involved.

Thus, according to another of its aspects, a subject of the invention is medicaments that comprise a compound of formula (I), or a pharmaceutically acceptable salt, or alternatively a hydrate or a solvate of the said compound.

These medicaments find their therapeutic use especially in the prevention and/or treatment of pain and inflammation, chronic pain, neuropathic pain (trauma-related, diabetic, metabolic, infection-related or toxic pain, or pain induced by an anticancer or iatrogenic treatment), (osteo)arthritic pain, rheumatic pain, fibromyalgia, back pain, cancer-related pain, facial neuralgia, headaches, migraine, dental pain, burns, sunburn, animal bites or insect bites, post-herpetic neuralgia, muscular pain, trapped nerves (central and/or peripheral), spinal column and/or brain trauma, ischaemia (of the spinal column and/or the brain), neurodegeneration, hemorrhagic strokes (of the spinal column and/or of the brain) and post-stroke pain.

The compounds of the invention may also be used for preventing and/or treating metabolic disorders such as diabetes.

The compounds of the invention may be used for the preparation of a medicament for preventing and/or treating urological disorders such as hyperactivity of the bladder, vesical hyperreflexia, vesical instability, incontinence, urgent micturition, urinary incontinence, cystitis, nephritic colic, pelvic hypersensitivity and pelvic pain.

The compounds of the invention may be used to prepare a medicament for preventing and/or treating gynecological disorders, for instance vulvodynia and pain associated with salpingitis or with dysmenorrhea.

These products may also be used for the preparation of a medicament for preventing and/or treating gastrointestinal disorders such as gastroesophageal reflux disorder, stomach ulcers, duodenal ulcers, functional dyspepsia, colitis, IBS, Crohn's disease, pancreatitis, oesophagitis and biliary colic.

Similarly, the products of the present invention may be useful in the prevention and/or treatment of respiratory disorders such as asthma, coughing, COPD, bronchoconstriction and inflammatory disorders. These products may also be used for preventing and/or treating psoriasis, pruritus, dermal, ocular or mucous irritation, herpes and zona.

The compounds of the invention may also be used for treating depression.

The compounds of the invention may also be used for treating central nervous system diseases such as multiple sclerosis.

According to another of its aspects, the present invention relates to pharmaceutical compositions comprising, as active principle, a compound according to the invention.

These pharmaceutical compositions contain an effective dose of at least one compound according to the invention or a pharmaceutically acceptable salt, a hydrate or a solvate of the said compound and also at least one pharmaceutically acceptable excipient.

The said excipients are chosen, according to the pharmaceutical form and the desired mode of administration, from the usual excipients known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or the possible salt, solvate or hydrate thereof, may be administered in a unit administration form, as a mixture with standard pharmaceutical excipients, to man and animals for the prophylaxis or treatment of the disorders or diseases mentioned above.

The appropriate unit forms of administration include oral forms such as tablets, soft or hard gel capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms and implants. For topical application, the compounds according to the invention may be used in creams, gels, pomades or lotions.

By way of example, a unit form of administration of a compound according to the invention in tablet form may comprise the following components:

| | |
|---|---|
| Compound according to the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

The said unit forms are dosed to allow a daily administration of from 0.001 to 30 mg of active principle per kg of body weight, according to the galenical form.

There may be particular cases in which higher or lower dosages are appropriate: such dosages do not depart from the scope of the invention. According to the usual practice, the dosage that is appropriate for each patient is determined by the doctor according to the mode of administration, the weight and the response of the said patient.

According to another of its aspects, the present invention also relates to a method for treating the pathologies indicated above, which comprises the administration to a patient of an effective dose of a compound according to the invention, or a pharmaceutically acceptable salt, or hydrate or solvate thereof.

What is claimed is:

1. A compound of the formula (I):

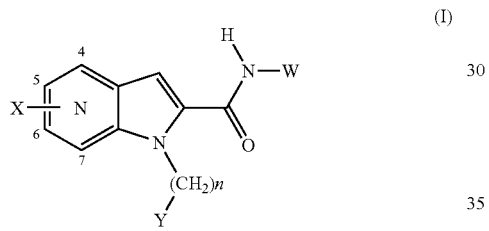

in which n is equal to 0, 1, 2 or 3;

the pyrrolopyridine nucleus is a pyrrolo[3,2-b]pyridine group, a pyrrolo[3,2-c]pyridine group, a pyrrolo[2,3-c]pyridine group or a pyrrolo[2,3-b]pyridine group;

the pyrrolopyridine nucleus being optionally substituted in the carbon position 4, 5, 6 or 7 with one or more substituents X, which may be identical or different, chosen from halogen, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkoxy, $C_3$-$C_7$-cycloalkyl-$C_1$-$C_3$-alkylene-O—, $C_1$-$C_6$-fluoroalkoxy, cyano, C(O)NR$_1$R$_2$, nitro, NR$_1$R$_2$, $C_1$-$C_6$-thioalkyl, —S(O)—$C_1$-$C_6$-alkyl, —S(O)$_2$—$C_1$-$C_6$-alkyl, SO$_2$NR$_1$, R$_2$, NR$_3$COR$_4$, NR$_3$SO$_2$R$_5$, aryl, aryl-$C_1$-$C_5$-alkylene, heteroaryl and heteroaryl-$C_1$-$C_5$-alkylene groups, the aryl or the heteroaryl being optionally substituted with one or more substituents chosen from halogen, $C_1$-$C_6$-alkyl, $C_3$-$C_7$-cycloalkyl, $C_3$-$C_7$-cycloalkyl-$C_1$-$C_3$-alkylene-O—, $C_1$-$C_6$-fluoroalkyl, $C_1$-$C_6$-alkoxy, $C_3$-$C_7$-cycloalkoxy, $C_3$-$C_7$-cycloalkyl-$C_1$-$C_3$-alkylene-O—, $C_1$-$C_6$-fluoroalkoxy, nitro or cyano groups;

Y represents a heteroaryl optionally substituted with one or more groups chosen from halogen, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, hydroxyl, $C_1$-$C_6$-alkoxy, $C_3$-$C_7$-cycloalkoxy, $C_3$-$C_7$-cycloalkyl-$C_1$-$C_6$-alkylene-O—, $C_1$-$C_6$-fluoroalkoxy, cyano, C(O)NR$_1$R$_2$, nitro, NR$_1$R$_2$, $C_1$-$C_6$-thioalkyl, $C_1$-$C_6$-thiofluoroalkyl, thiol, —S(O)—$C_1$-$C_6$-alkyl, —S(O)—$C_3$-$C_7$-cycloalkyl, —S(O)—$C_1$-$C_6$-alkylene-$C_3$-$C_7$-cycloalkyl, —S(O)$_2$—$C_1$-$C_6$-alkyl, —S(O)$_2$—$C_3$-$C_7$-cycloalkyl, —S(O)$_2$—$C_1$-$C_6$-alkylene-$C_3$-$C_7$-cycloalkyl SO$_2$NR$_1$, R$_2$, NR$_3$COR$_4$, NR$_3$SO$_2$R$_5$, aryl, aryl-$C_1$-$C_5$-alkylene, heteroaryl or heteroaryl-$C_1$-$C_5$-alkylene groups, the aryl or the heteroaryl being optionally substituted with one or more substituents chosen from a halogen and $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkoxy, $C_3$-$C_7$-cycloalkyl-$C_1$-$C_6$-alkylene-O—, $C_1$-$C_6$-fluoroalkoxy, nitro or cyano groups; wherein R$_1$ and R$_2$, represent, independently of each other, hydrogen, $C_1$-$C_6$-alkyl, $C_3$-$C_7$-cycloalkyl, $C_3$-$C_7$-cycloalkyl-$C_1$-$C_3$-alkylene, aryl, aryl-$C_1$-$C_5$-alkylene, heteroaryl or heteroaryl-$C_1$-$C_5$-alkylene group, the aryl or the heteroaryl being optionally substituted with one or more substituents chosen from halogen, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkoxy, $C_3$-$C_7$-cycloalkyl-$C_1$-$C_6$-alkylene-O—, $C_1$-$C_6$-fluoroalkoxy, nitro or cyano groups;

or R$_1$ and R$_2$ taken together with the nitrogen atom to which they are attached form azetidine, pyrrolidine, piperidine, azepine, morpholine, thiomorpholine, piperazine or homopiperazine group, this group being optionally substituted with a $C_1$-$C_6$-alkyl, $C_3$-$C_7$-cycloalkyl, $C_3$-$C_7$-cycloalkyl-$C_1$-$C_3$-alkylene, aryl, aryl-$C_1$-$C_5$-alkylene, heteroaryl or heteroaryl-$C_1$-$C_5$-alkylene group, the aryl or the heteroaryl being optionally substituted with one or more substituents chosen from halogen, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkoxy, $C_3$-$C_7$-cycloalkyl-$C_1$-$C_6$-alkylene-O—, $C_1$-$C_6$-fluoroalkoxy, nitro or cyano groups;

R$_3$ and R$_4$ represent, independently of each other, hydrogen, $C_1$-$C_6$-alkyl, $C_3$-$C_7$-cycloalkyl, $C_3$-$C_7$-cycloalkyl-$C_1$-$C_3$-alkylene, aryl, aryl-$C_1$-$C_5$-alkylene, heteroaryl or heteroaryl-$C_1$-$C_5$-alkylene group, the aryl or the heteroaryl being optionally substituted with one or more substituents chosen from halogen, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkoxy, $C_3$-$C_7$-cycloalkyl-$C_1$-$C_6$-alkylene-O—, $C_1$-$C_6$-fluoroalkoxy, nitro or cyano groups;

R$_5$ represents $C_1$-$C_6$-alkyl, $C_3$-$C_7$-cycloalkyl, $C_3$-$C_7$-cycloalkyl-$C_1$-$C_3$-alkylene, aryl, aryl-$C_1$-$C_5$-alkylene, heteroaryl or heteroaryl-$C_1$-$C_5$-alkylene group, the aryl or the heteroaryl being optionally substituted with one or more substituents chosen from halogen, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkoxy, $C_3$-$C_7$-cycloalkyl-$C_1$-$C_6$-alkylene-O—, $C_1$-$C_6$-fluoroalkoxy, nitro or cyano groups;

W represents a fused bicyclic group of formula:

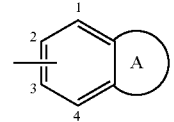

linked to the nitrogen atom via positions 1, 2, 3 or 4;

A represents a 5- to 7-membered heterocycle comprising from one to three heteroatoms chosen from O, S and N;

the carbon atom(s) of A being optionally substituted with one or more groups chosen from hydrogen, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl, aryl-$C_1$-$C_5$-alkylene, heteroaryl or heteroaryl-$C_1$-$C_5$-alkylene, oxo or thio groups; the aryl or the heteroaryl being optionally substituted with one or more substituents chosen from halogen, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkoxy, $C_3$-$C_7$-cycloalkyl-$C_1$-$C_6$-alkylene-O—, $C_1$-$C_6$-fluoroalkoxy, nitro or cyano groups;

the nitrogen atom(s) of A being optionally substituted with $R_6$ when the nitrogen is adjacent to a carbon atom substituted with an oxo group, or with $R_7$ in the other cases; wherein $R_6$ represents hydrogen, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl, aryl-$C_1$-$C_5$-alkylene, heteroaryl or heteroaryl-$C_1$-$C_5$-alkylene group, the aryl or the heteroaryl being optionally substituted with one or more substituents chosen from halogen, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxy, $C_3$-$C_7$-cycloalkoxy, $C_3$-$C_7$-cycloalkyl-$C_1$-$C_6$-alkylene-O—, $C_1$-$C_6$-fluoroalkoxy, nitro or cyano groups; and $R_7$ represents hydrogen, $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, aryl-$C_1$-$C_6$-alkylene, $C_1$-$C_6$-alkyl-C(O)—, $C_3$-$C_7$-cycloalkyl-$C_1$-$C_3$-alkylene-(CO)—, $C_1$-$C_6$-fluoroalkyl-C(O)—, $C_3$-$C_7$-cycloalkyl-C(O)—, aryl-C(O)—, aryl-$C_1$-$C_6$-alkylene-C(O)—, $C_1$-$C_6$-alkyl-S(O)$_2$—, $C_1$-$C_6$-fluoroalkyl-S(O)$_2$—, $C_3$-$C_7$-cycloalkyl-S(O)$_2$—, $C_3$-$C_7$-cycloalkyl-$C_1$-$C_3$-alkylene-S(O)$_2$—, aryl-S(O)$_2$— or aryl-$C_1$-$C_6$-alkylene-S(O)$_2$— or aryl group; and wherein the sulfur atom(s) of the heterocycle A optionally being in oxidized form;

the nitrogen atom(s) of the heterocycle A optionally being in oxidized form; and the nitrogen atom in position 4, 5, 6 or 7 of the pyrrolopyridine optionally being in oxidized form;

or a salt thereof.

2. The compound of formula (I) according to claim 1, wherein n is equal to 0 or 1 or a salt thereof.

3. The compound of formula (I) according to claim 2, wherein the pyrrolopyridine nucleus is a pyrrolo[3,2-b]pyridine group, a pyrrolo[3,2-c]pyridine group, a pyrrolo[2,3-c]pyridine group or a pyrrolo[2,3-b]pyridine group; and the pyrrolopyridine nucleus being optionally substituted in carbon position 4, 5, 6 or 7 with one or more substituents X, which may be identical or different, chosen from halogen, $C_1$-$C_6$-alkyl and $C_1$-$C_6$-fluoroalkyl groups; or a salt thereof.

4. The compound of formula (I) according to claim 1, wherein the pyrrolopyridine nucleus is a pyrrolo[3,2-b]pyridine group, a pyrrolo[3,2-c]pyridine group, a pyrrolo[2,3-c]pyridine group or a pyrrolo[2,3-b]pyridine group; and the pyrrolopyridine nucleus being optionally substituted in carbon position 5 with a substituent X as defined in the general formula (I) according to claim 1; or a salt thereof.

5. The compound of formula (I) according to claim 1, wherein the pyrrolopyridine nucleus is a pyrrolo[2,3-b]pyridine group optionally substituted in carbon position 4, 5, 6 or 7 with one or more substituents X, which may be identical or different, chosen from halogen or $C_1$-$C_6$-fluoroalkyl; or a salt thereof.

6. The compound of formula (I) according to claim 5, wherein the pyrrolopyridine nucleus is a pyrrolo[2,3-b]pyridine group optionally substituted in carbon position 5 with a substituent X chosen from halogen or $C_1$-$C_6$-fluoroalkyl; or a salt thereof.

7. The compound of formula (I) according to claim 1, wherein Y represents a group chosen from imidazolyl, thiazolyl, oxazolyl, furyl, thiophenyl, oxadiazolyl, tetrazolyl, pyridyl, pyrazinyl, pyrimidinyl, pyridazinyl, indolyl, benzofuryl, benzothiophenyl, benzoxazolyl, benzimidazolyl, indazolyl, benzothiazolyl, isobenzothiazolyl, benzotriazolyl, quinolyl, isoquinolyl, quinoxalinyl, cinnolinyl, quinazolinyl, phthalazinyl and naphthyridinyl groups; this group being optionally substituted; or a salt thereof.

8. The compound of formula (I) according to claim 7, wherein Y represents pyridyl; or a salt thereof.

9. The compound of formula (I) according to claim 1, wherein W is chosen from indolinyl, isoindolinyl, indolyl, isoindolyl, benzofuryl, dihydrobenzofuryl, benzothiophenyl, dihydrobenzothiophenyl, benzoxazolyl, dihydrobenzoxazolinyl, isobenzofuryl, dihydroisobenzofuryl, benzimidazolyl, dihydrobenzimidazolyl, indazolyl, benzothiazolyl, isobenzothiazolyl, dihydroisobenzothiazolyl, benzotriazolyl, quinolyl, dihydroquinolyl, tetrahydroquinolyl, isoquinolyl, dihydroisoquinolyl, tetrahydroisoquinolyl, benzoxazinyl, dihydrobenzoxazinyl, benzothiazinyl, dihydrobenzothiazinyl, cinnolinyl, quinazolinyl, dihydroquinazolinyl, tetrahydroquinazolinyl, quinoxalinyl, dihydroquinoxalinyl, tetrahydroquinoxalinyl, phthalazinyl, dihydrophthalazinyl, tetrahydrophthalazinyl, tetrahydrobenz[b]azepinyl, tetrahydrobenz[c]azepinyl, tetrahydrobenz[d]azepinyl, tetrahydrobenzo[b][1,4]diazepinyl, tetrahydrobenzo[e][1,4]diazepinyl, tetrahydrobenzo[b][1,4]oxazepinyl and tetrahydrobenzo[b][1,4]thiazepinyl groups; these groups being optionally substituted; or a salt thereof.

10. The compound of formula (I) according to claim 9, wherein W represents benzimidazolyl or benzothiazolyl, the carbon atom(s) of W being optionally substituted with one or more $C_1$-$C_6$-alkyl groups; the nitrogen atom(s) of W being optionally substituted with a $C_1$-$C_6$-alkyl group; or a salt thereof.

11. A process for preparing a compound of formula (I) according to claim 1 comprising:

reacting a compound of formula (IV):

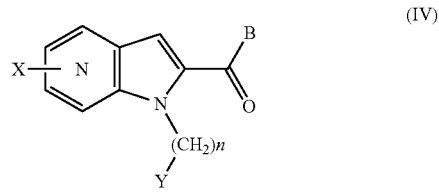

in which n, X and Y are as defined in claim 1 and B represents a $C_1$-$C_4$-alkoxy group, with an amide of the compound of formula (V):

in which W is as defined in claim 1, at the reflux point of a solvent, and wherein the amide of the compound of formula (V) being prepared via the prior action of trimethylaluminum on the compound of general formula (V).

12. A process for preparing a compound of formula (I) according to claim 1 comprising:
converting a compound of formula (IV):

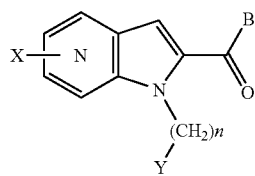

in which n, X and Y are as defined in claim 1 and B represents a hydroxyl group,
into the acid chloride via the action of thionyl chloride at the reflux point of a solvent in the presence of a base; and
reacting the resulting acid chloride with the compound of formula (V):

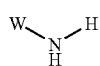

in which W is as defined in claim 1; or alternatively
carrying out a coupling reaction between a compound of formula (IV) in which n, X and Y are as defined in claim 1 and B represents a hydroxyl group,
with the compound of formula (V), in which W is as defined in claim 1, in the presence of a coupling agent and a base, in a solvent.

13. A pharmaceutical composition comprising a compound of formula (I) according to claim 1 or a pharmaceutically acceptable salt thereof and at least one pharmaceutically acceptable excipient.

14. A pharmaceutical composition comprising a compound of formula (I) according to claim 2 or a pharmaceutically acceptable salt thereof and at least one pharmaceutically acceptable excipient.

15. A pharmaceutical composition comprising a compound of formula (I) according to claim 3 or a pharmaceutically acceptable salt thereof and at least one pharmaceutically acceptable excipient.

16. A pharmaceutical composition comprising a compound of formula (I) according to claim 4 or a pharmaceutically acceptable salt thereof and at least one pharmaceutically acceptable excipient.

17. A pharmaceutical composition comprising a compound of formula (I) according to claim 5 or a pharmaceutically acceptable salt thereof and at least one pharmaceutically acceptable excipient.

18. A pharmaceutical composition comprising a compound of formula (I) according to claim 6 or a pharmaceutically acceptable salt thereof and at least one pharmaceutically acceptable excipient.

19. A pharmaceutical composition comprising a compound of formula (I) according to claim 7 or a pharmaceutically acceptable salt thereof and at least one pharmaceutically acceptable excipient.

20. A pharmaceutical composition comprising a compound of formula (I) according to claim 8 or a pharmaceutically acceptable salt thereof and at least one pharmaceutically acceptable excipient.

21. A pharmaceutical composition comprising a compound of formula (I) according to claim 9 or a pharmaceutically acceptable salt thereof and at least one pharmaceutically acceptable excipient.

22. A pharmaceutical composition comprising a compound of formula (I) according to claim 10 or a pharmaceutically acceptable salt thereof and at least one pharmaceutically acceptable excipient.

23. A method of treating a disease in a patient, which disease is selected from the group consisting of pain, inflammation, metabolic disorders, urological disorders, gynecological disorders, gastrointestinal disorders, respiratory disorders, psoriasis, pruritus, dermal, ocular or mucous irritations, herpes, zona, multiple sclerosis and depression, comprising administering to said patient a therapeutically effective amount of a compound of formula (I) according to claim 1.

* * * * *